United States Patent [19]

Kanner et al.

[11] Patent Number: 4,579,965

[45] Date of Patent: Apr. 1, 1986

[54] PROCESS FOR PREPARING VINYL-TRI-(TERTIARY SUBSTITUTED) ALKOXYSILANES

[75] Inventors: Bernard Kanner, West Nyack; Jennifer M. Quirk, Bedford Hills; Arthur P. De Monte, Brooklyn, all of N.Y.

[73] Assignee: Union Carbide Corporation, Danbury, Conn.

[21] Appl. No.: 694,306

[22] Filed: Jan. 24, 1985

[51] Int. Cl.[4] .................... C07F 7/09; C07F 7/08; C07F 7/18
[52] U.S. Cl. ........................................ 556/479
[58] Field of Search .................................. 556/479

[56] References Cited

U.S. PATENT DOCUMENTS

| | | | |
|---|---|---|---|
| 2,823,218 | 2/1958 | Speier et al. | 260/448.2 |
| 2,851,473 | 9/1958 | Wagner et al. | 556/479 |
| 3,404,169 | 10/1968 | Gaignon et al. | 556/479 |
| 3,445,425 | 5/1969 | Speier | 260/46.5 |
| 3,485,857 | 12/1969 | Speier | 260/429 |
| 3,793,358 | 2/1974 | Bauer et al. | 556/479 |

FOREIGN PATENT DOCUMENTS 57-4995  1/1982  Japan ................... 556/479

OTHER PUBLICATIONS

E. Lukevics, *Russ. Chem. Rev.*, 46, 264 (1977).
K. A. Andrianov, et al., *Isv. Akad. Nauk SSSR, Ser. Khim.* 1968, pp. 351–356.
K. A. Andrianov, et al., *Isv. Akad. Nauk SSSR, Ser. Khim.* 1969, pp. 1539–1545.
E. P. Lebedev and V. O. Reikhsfel'd, *Zhur, Obshch. Khim*, 38 655, (1968).
E. P. Lebedev and V. O. Reikhsfel'd, *Zhur, Obshch. Khim*, 40, 1082, (1970).
W. B. Dennis and J. L. Speier, *J. Org. Chem.*, 35, 3879 (1970).
I. M. Gverdtsiteli, et al., *Soobshch Akad. Nauk Gruz. SSR*, 84, 381 (1976).
I. M. Gverdtsiteli, et al., *Tezisy Dokl-Vses. Konf. Khim. Atsetilena*, 5th 1975, 172.

*Primary Examiner*—Paul F. Shaver
*Attorney, Agent, or Firm*—Paul W. Leuzzi, II

[57] ABSTRACT

A process for preparing vinyl-tri-t-oxysilanes by reacting a tri-t-alkoxysilane with an alkyne in the presence of a platinum hydrosilation catalyst at a reaction temperature greater than 150° C. forms a vinyl-tri-t-alkoxysilane in high yields and of high quality.

12 Claims, No Drawings

PROCESS FOR PREPARING VINYL-TRI-(TERTIARY SUBSTITUTED) ALKOXYSILANES

BACKGROUND OF THE INVENTION

1. Field of the Invention

The present invention relates to an improved process for the preparation of vinyl-tri-(tertiary-substituted)-alkoxysilanes and, in particular, to a hydrosilation process for producing a high yield of vinyl-tri-(tertiary-alkoxy) silanes of high purity.

2. Description of the Prior Art

The hydrosilation reaction was discovered about 1947 and, over the years, has become one of the best known and most widely practiced reactions in organosilicon chemistry. It enjoys a broad spectrum of large scale commercial applications and has been the subject of thousands of publications and extensive reviews, including the following monographs:

E. Lukevics and M. G. Voronkov, Organic Insertion Reactions of Group II Elements, Consultants Bureau, N.Y., 1966;

C. Eaborn and R. W. Boh, Organometallic Compounds of the Group IV Elements, Dekker, N.Y., 1968, Vol. I;

M. G. Pomerantseva et al, Preparation of Carbafunctional Organosilanes by an Addition Reaction, Moscow, 1971;

E. Lukevics, Russ. Chem Rev., 46, 264 (1977) and

E. Lukevics et al, J. Organometal Chem. Library 5, 1977, pp. 1-179.

Various classes of platinum compounds have been found to be effective hydrosilation catalysts. Chloroplatinic acid, which is a soluble form of platinum, has proved to be an especially effective hydrosilation catalyst, as disclosed in U.S. Pat. No. 2,823,218 issued Feb. 11, 1958.

In U.S. Pat. No. 2,637,738, issued May 5, 1953 it has been proposed to react triethoxysilane with acetylene in the presence of a platinum black catalyst at temperatures of 130° C. and pressures of 20 atmospheres to form vinyltriethoxysilane. In this reaction yields were said to be relatively low and a substantial quantity of 1,2-bis(-triethyoxysilyl)ethane by-product was also produced.

Japanese Pat. No. 57-04996, issued Jan. 11, 1982 discloses that acetylene can be reacted with trialkoxysilanes in the presence of chloroplatinic acid at reaction temperatures less than about 180° C. The major product formed was 1,2-bis(trialkoxysilyl)ethane. With a platinum halide phosphine catalyst, PtX$_2$(PPh$_3$)$_2$, the trialkoxysilanes reacted with acetylene to provide major amounts of vinyltrialkoxysilanes and significant and unacceptable amounts of undesired by-products, such as 2-bis(trialkoxysilyl)ethanes.

The art has recognized to the desirability of providing a process to produce high yields of relatively pure vinyl-tri-(tertiary substituted)alkoxysilanes and, especially, vinyl-tri-(tert-alkoxy)silanes for use as intermediates and reactive coupling agents by hydrosilation techniques. However, the hydrosilation techniques disclosed in the art have not contemplated producing such tertiary alkoxysilanes. In general, the prior art techniques, as they relate to hydrosilation of tri-(primary)-alkoxysilanes and tri-(secondary)-alkoxysilanes, have taught that reaction temperatures should be on the order of less than about 180° C. and that undesired by-products, especially bis(trialkoxysilyl)ethanes, are invariably produced.

As set forth herein the tri-tertiary substituted alkoxysilanes of the invention are referred to as tri-t-alkoxysilanes and the tri-tertiary-alkoxysilanes of the invention are referred to hereafter as tri-t-alkoxysilanes.

SUMMARY OF THE INVENTION

The present invention is a process for preparing vinyl tri-t-alkoxysilanes by reacting a tri-t-alkoxysilane of the general formula I:

HSi(OCRR'R")$_3$       [I]

with an alkyne of the general formula II:

R'''C≡CH       [II]

wherein R''' is hydrogen, a saturated or unsaturated aliphatic hydrocarbon radical or an aromatic hydrocarbon radical, R, R' and R" are the same or different and are each a saturated or unsaturated aliphatic hydrocarbon radical or an aromatic hydrocarbon radical in the presence of a platinum hydrosilation catalyst at a reaction temperature greater than 150° C. to form a vinyl-tri-t-alkoxysilane of the general formula III:

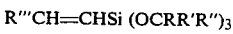

R'''CH=CHSi (OCRR'R")$_3$       [III]

wherein R, R' R" and R''' are as before.

It has been found that the temperature of the reaction should be maintained at least about 150° C. to provide high yields of the desired product. At lower reaction temperatures the yields of the desired product are substantialy reduced. In addition, it is an important and unexpected feature of the process of the invention that the amount of undesired by-products produced, such as bis(trialkoxysilyl)ethane is very low.

DESCRIPTION OF THE PREFERRED EMBODIMENTS

The tri-t-alkoxysilane reactants employed in the present invention are of the general formula (I):

HSi(OCRR'R")$_3$       [I]

wherein R,R' and R" are the same or different and are each a saturated or unsaturated aliphatic hydrocarbon radical or an aromatic hydrocarbon radical.

Typical examples of R, R' and R" are alkyl radicals, such as methyl, ethyl, propyl, isopropyl, butyl, isobutyl, pentyl, isopentyl, neopentyl, hexyl, octyl, dodecyl, octadecyl, 3-methyl heptyl, 6-butyloctadecyl, tertiary butyl and 2,2-diethylpentyl; alkenyl radicals, such as allyl, hexenyl, butenyl, 3-octenyl, 4,9-octadecadienyl and 4-nonenyl; alkynyl radicals, such as propynyl, heptynyl, butynyl, decynyl and alkenynyl radicals, such as 1-penten-3-ynyl and 2-ethyl-1-buten-3-ynyl; cycloaliphatic radicals, such as cyclobutyl, cyclopentyl, cyclohexyl, cycloheptyl, propylcyclohexyl, 2,4-dimethylcyclopentyl, cyclohexenyl, bicyclo(3.1.0)hexyl, tricyclo(3.2.1.1$^{3,8}$)-5-nonenyl, spiro[4.5]decyl, dispiro(4.1.4.2)-1-tridecenyl, decahydronaphthyl, 2.3-dihydroindyl and 1,2,3,4-tetrahydronaphthyl and aryl radicals, such as phenyl, tolyl, xylyl, 3-ethylphenyl, naphthyl, pentaphenyl, 3,4-methylethyl-phenyl, 2-phenyl-octyl, 3-methyl-2-(4-isopropylphenyl)heptyl, benzyl, 2-ethyl-tolyl, 2-ethyl-p-cymenyl, diphenyl-methyl, 4,5-diphenylpentyl, 4-m-terphenyl, 9,9-bifluoryl and beta-phenylethyl.

In addition, any combination of R, R' and R" can together form either a cyclic radical or a fused cyclic radical together with the carbon (C) atom of the formula I compounds as long as the carbon (C) atom is tertiary substituted. The cyclic and fused cyclic radicals are as listed above.

Typical examples of the tri-t-alkoxysilanes of the invention include:

HSi[OC(C$_2$H$_5$)$_3$]$_3$;
HSi[OC(C$_3$H$_7$)$_3$]$_3$;
HSi[OC(CH$_3$)(C$_4$H$_9$)$_2$]$_3$;
HSi[OC(CH$_3$)(C$_3$H$_7$)(C$_4$H$_9$)]$_3$;
HSi[OC(CH$_3$)$_3$]$_3$;
HSi[OC(CH$_3$)(C$_2$H$_5$)$_2$]$_3$;
HSi[OC(CH$_3$)$_2$(C$_2$H$_5$)]$_3$;
HSi[OC(C$_2$H$_5$)$_2$(CH$_2$CH=CH$_2$)]$_3$;

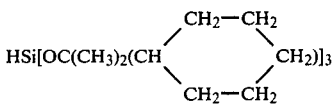

HSi[OC(CH$_3$)$_2$(C$_6$H$_5$)]$_3$;
HSi[OC(C$_6$H$_5$)$_3$]$_3$;

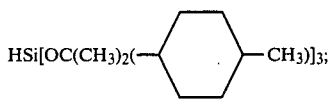

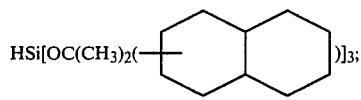

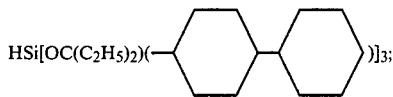

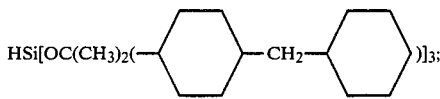

HSi(OC(CH$_3$)(C$_2$H$_5$)(C$_{12}$H$_{25}$)]$_3$;
HSi(OC(CH$_3$)$_2$(C$_{13}$H$_{27}$)]$_3$;
HSi[OC(CH$_3$)$_2$(CH$_2$CH=CH$_2$CH=CHCH$_3$)]$_3$
HSi[OC(C$_2$H$_5$)$_2$(CH$_3$C≡CH)]$_3$.

In general the preferred tri-t-alkoxysilanes of the invention are tri-t-alkoxysilanes in which R, R' and R" are each lower alkyl having from 1 to 6 carbon atoms. Especially preferred tri-t-alkoxysilanes of the invention include:
tri-t-butoxysilane, tri(2-methyl-2-butoxy)silane and tri(3-methyl-3-pentoxy)silane.

The alkynes of the invention which, in the presence of the hydrosilation catalyst of the invention, form vinyl adducts with the tri-t-alkoxysilanes of the invention, have the general formula II as follows:

R'''C≡CH wherein R''' is hydrogen or an aliphatic or aromatic hydrocarbon radical. Typical examples of such R''' radicals include: alkyl radicals having from about 1 to 20 carbon atoms such as methyl, ethyl, propyl, isopropyl, butyl, pentyl, hexyl, octyl, dodecyl, heptadecyl and eicosyl radicals, aryl radicals, such as phenyl, tolyl, xylyl, naphthyl, beta-phenylethyl, benzyl, 2-phenyloctyl, diphenyl-methyl and like radicals and cycloaliphatic radicals, such as cyclobutyl, cyclopentyl, cyclohexyl, propylcyclohexyl, bicyclo[3.1.0] hexyl, spiro[4.5] decyl and like radicals.

The preferred alkynes of the invention are those in which R''' is hydrogen, aryl or lower (C$_1$-C$_{10}$) alkyl.

The most preferred alkynes of the invention are acetylene, 1-hexyne, 1-octyne and phenylacetylene.

In general, the molar ratio of the tri-t-alkoxysilane reactant to the alkyne reactant should be 1:1 (or the stoichiometric ratio) to provide the best yields. However, the molar ratio may be greater or lesser than 1:1 if desired.

The reaction is carried out in the presence of a platinum hydrosilation catalyst of the invention. The platinum catalyst can be employed in a broad spectrum of forms. The catalyst can be platinum metal, either alone or on a support, such as carbon black or alumina. Soluble compounds of platinum or complexes of platinum are also employed as the platinum catalyst.

Typical soluble compounds of platinum are hexachloroplatinic acid and platinum (II) 2,4-pentanedionate. Solutions of hexachloroplatinic acid in organic solvents; such as alcohols, including methanol, ethanol, and isopropanol; ketones, such as cyclohexanone; ethers, as dimethyl ether of ethylene glycol or diethyleneglycol and esters as ethyl acetate or methyl benzoate, can also be utilized.

Platinum complexes combined with unsaturated compounds as ethylene, cyclohexene, styrene, alkylethylenes or such platinum complexes with phosphines, phosphines on polymeric carriers, cyclopropane and sulphoxides, can also be utilized.

If desired, bivalent and quadrivalent platinum complexes may also be employed. Platinum complexes on inorganic or organic polymeric carriers and polymeric platinum chelates are also possible forms for the platinum hydrosilation catalyst.

Usually, best results are obtained, and accordingly, it is preferred to employ as the hydrosilation catalyst, chloroplatinic acid, platinum (II) 2,4-pentanedionate or a platinum phosphine complex, as bis(triphenylphosphine)platinum (II) chloride and tetrakis(triphenylphosphine)platinum. Other useful forms of platinum catalysts will be apparent to those skilled in the art.

In general, the catalyst is employed in sufficient amounts to complete the reaction. Because platinum catalysts are expensive, it is usually best to employ them in amounts not in excess of that which is required to provide satisfactory yields. Accordingly, for this and other purposes it is preferred to employ from about $1 \times 10^{-6}$ mole percent to $5 \times 10^{-2}$ mole percent of platinum hydrosilation catalyst of the invention based on the amount of tri-t-alkoxysilane to be reacted.

The reaction temperature at which the process of the invention is carried out is very important. At reaction temperatures below about 150° C. it has been found that substantially reduced yields of vinylsilane adducts are obtained. At temperatures above about 150° C., however, the silicon-hydrogen bond adds readily across the alkyne bond in the presence of the hydrosilation catalyst to yield the vinylsilanes of the invention as follows:

$$R'''C{\equiv}CH + HSi(OCRR'R'')_3 \rightarrow R'''CH{=}C\text{-}HSi(OCRR'R'')_3$$

where R, R' R" and R'" are as before.

The amount of undesired by-products produced by the inventive process, such as bis(trialkoxysilyl)ethane, is insignificant, as compared to hydrosilation reactions of trichlorosilane and most trialkoxysilanes, which yield both vinylsilane and bis(silyl)ethane, especially when chloroplatinic acid is the hydrosilation catalyst. In general, the amount of by-products produced is usually less than 5%, and, most often, less than 3% by weight of the total yield of reaction product.

While the particular reasons for the enhanced reactivity of the tri-t-alkoxysilaness of the invention toward hydrosilation at the elevated reaction temperatures of at least about 150° C. is not completely understood, it is believed that at such higher temperatures an intermediate platinum-silicon catalytic complex is more readily formed, while at lower temperatures the tri-t-alkoxysilane forms the desired catalytic intermediate complex, very slowly.

Another unexpected feature of the present process is that there does not seem to be any significant catalyst degradation at the elevated reaction temperatures. That feature is evidence that the platinum tri-t-alkoxysilane catalytic intermediates are relatively stable and contribute significantly to the high efficiency of the instant process. The vinylalkoxysilane product yield of the instant process is high. Usually product yields are at least about 95% of theoretical and, most often, over 98% of theoretical.

In general, the upper reaction temperature of the present invention is determined by the decomposition temperature of either the starting materials or the reaction product. For most purposes it is preferred to maintain the reaction temperature from about 180° C. to 250° C.

The reaction pressure is not critical. The process is usually conducted at atmospheric or superatmospheric pressures. If desired, the reaction is conducted at alkynyl gas inlet pressures, which are greater than atmospheric.

The reaction time is not a significant factor in the process. In general, the reaction is completed in from about 1 to 3 hours.

The reaction may be carried out in the absence or presence of a reaction solvent. If it is desired to enhance the solubility of the reactants or to provide a heat sink to help maintain proper temperature control, a solvent can be employed. Typical reaction solvents include hydrocarbon solvents, such as octane, xylene or, preferably, triisopropylbenzene.

In order to conduct the process of the invention the reactants are added in any appropriate order. Generally, the platinum catalyst is added to the tri-t alkoxysilane reactant, the reaction mix heated to the desired reaction temperature and then the alkyne reactant, such as acetylene gas, is fed into the reaction mix at a constant rate until addition is complete. The product is recovered and analyzed by conventional procedures.

When all the reactants are liquids, the reactants are added to an autoclave, the autoclave is sealed and the contents heated until the reaction is complete.

The following examples illustrate certain preferred embodiments of the invention under laboratory conditions and are not intended to limit the scope of the invention.

EXAMPLE 1

A 500 ml 3-neck flask was equipped with a stopper, Claisen adapter, thermometer and stirring bar. A septum was wired to the Claisen adapter and a water condenser and a Dewar condenser attached to the side arm. Into the flask was introduced 100 g (0.49 mol.) of triisopropylbenzene solvent and 30 g (0.19 mol.) of tri-tert-butoxysilane. Into this mix was added 60 ppm (120 μl of 15 mg Pt/ml) chloroplatinic acid. The reaction mix was heated to 220° C. in an oil bath and acetylene was fed into the reaction mix with a stainless steel twelve inch needle at a rate of 75–100 cc/min. with a back pressure of 4–5 psig. After one hour the hydrosilation reaction was complete as determined by GPC. The single product formed was vinyltri-tertbutoxysilane in amounts greater than 90% of the theoretical yield.

EXAMPLE 2

The reaction was carried out in accordance with the procedure of Example 1, except that bis(triphenylphosphine)platinum (II) chloride was used as the platinum hydrosilation catalyst. The single product formed was vinyltri-tertbutoxysilane.

COMPARATIVE EXAMPLE 1

The reaction was carried out in accordance with the procedure of Example 1 except that a reaction temperature of only 135° C. was maintained. After two hours only 5% of the vinyl-t-butoxysilane had formed. This run demonstrates the criticality of maintaining the reaction temperature of at least about 150° C.

EXAMPLE 3

A 50 ml Schlenk tube was equipped with a Claisen adapter and stirring bar. A septum was wired to the Claisen adapter and a water condenser attached to the side arm. In the flask was placed 5 g (0.025 mol.) of triisopropylbenzene and 5 g (0.017 mol) tri(2-methyl-2-butoxy)silane. Into this mix was added 30 ppm (10 ml of 15 mg Pt/ml)chloroplatinic acid. The reaction mixture was heated to between 200°–235° C. in an oil bath and acetylene was fed into the reaction mix with a stainless steel 12 inch needle at a rate of 50 cc/min with a back pressure of 4–5 psig. After three hours the hydrosilation was complete as determined by GPC. The single product was determined to be vinyl tri-(2-methyl-2-butoxy)-silane in a yield greater than 90% of theoretical.

EXAMPLE 4

A 50 ml Schlenk tube was equipped with a Claisen adapter and stirring bar. A septum was wired to the Claisen adapter and a water condenser and a Dewar condenser attached to the side arm. In the flask was placed 5 g (0.025 mol.) of triisopropylbenzene and 5 g (0.015 mol.) of tri(3-methyl-3-pentoxy)silane. Into this mix was added 30 ppm (10 ml of 15 mg Pt/ml) chloroplatinic acid. The reaction mixture was heated to between 200°–240° C. in an oil bath and acetylene was fed into the mix with a stainless steel 12 inch needle at a rate of 50 cc/min with a back pressure of 4–5 psig. After three hours the hydrosilation was complete as determined by GPC. The single product was vinyltri-(3-methyl-3-pentoxy)silane in a yield greater than 90% of theoretical.

COMPARATIVE EXAMPLE 2

A 50 ml Schlenk tube with a side arm was equipped with a Claisen adapter and stirring bar. A septum was wired to the Claisen adapter and a water condenser was also attached. Into the flask was placed 5 g (0.041 mol.) trimethoxysilane and 1 g triisopropylbenzene. To this solution was also added 30 ppm of $H_2PtCl_6$ (10 ml; 15 mg Pt/ml). The reaction mix was heated to only 120° C. in an oil bath and acetylene was bubbled into the reaction mix with a stainless steel needle at a rate of 50 cc/min with a back pressure maintained of 4–5 psig. After one hour the reaction was complete as monitored by GPC. The major product formed was 1,2-bis(trimethoxysilyl)ethane (76%). Vinyltrimethoxysilane (22%) and tetramethoxysilane (2%) were also produced.

The trimethoxysilane employed in this test had a primary alkyl group, not a tertiary group, and the reaction temperature was well below the temperature required by the process of the invention. Under such conditions, the bis-silyl derivative predominated.

COMPARATIVE EXAMPLE 3

The reaction was carried out in accordance with the procedure of Comparative Example 2, except that the silane used was triethoxysilane and the reaction temperature was 150° C. The reaction was monitored by GPC and was completed in one hour. The major product formed was 1,2-bis(triethoxysilyl)ethane (72%), with vinyltriethoxysilane (25%) and tetraethoxysilane also being formed (3%). With a primary alkyl silane and at lower reaction temperatures, the undesired bis(silyl)ethane was the main reaction product.

COMPARATIVE EXAMPLE 4

The reaction was carried out in accordance with the procedure of Comparative Example 2, except that triisopropoxysilane (a secondary alkoxysilane) was used as the starting silane and the reaction temperature was maintained at 180° C. After one and a half hours the reaction was complete as monitored by GPC. The products formed were 1,2-bis(triisopropoxysilyl)ethane (78%), vinyltriisopropoxysilane (21%) and tetraisopropoxysilane (1%). Even at high reaction temperatures, the bis-silyl derivative predominated, where the starting silane was other than a tertiary-oxysilane.

COMPARATIVE EXAMPLE 5

A 50 ml Schlenk tube with a side arm was equipped with a Claisen adapter and stirring bar. To the Claisen adapter was wired a septum and a water condenser was also attached. 5 g (0.041 mol.) of trimethoxysilane, 1 g triisopropylbenzene and 30 ppm (0.064 mg) $PtCl_2(PPh_3)_2$ was introduced into the flask. The reaction mix was heated to 130° C. in an oil bath and acetylene was fed into the reaction mix with a stainless steel 12 inch needle at a rate of 50 cc/min with back pressure maintained at 4–5 psig. After one hour the hydrosilation was completed as determined by GPC. The products formed were vinyltrimethoxysilane (82%), 1,2-bis(trimethoxysilyl)ethane (16%) and tetramethoxysilane (2%).

The results show that the yield of vinyl addition product increased with the use of a phosphine-complexed platinum catalyst. In this Comparative Example, which employed a primary alkoxysilane, a significant amount of undesired by-product was formed, however.

COMPARATIVE EXAMPLE 6

The reaction was carried out as in Comparative Example 5, except that triethoxysilane was used as the starting silane. The reaction as monitored by GPC and was complete in two hours. Vinyltriethoxysilane (79%) was the major product formed and significant amounts of 1,2-bis(triethoxysilyl)ethane (13%) and tetraethoxysilane (8%) by-products, were also formed.

COMPARATIVE EXAMPLE 7

The reaction was carried out as in Comparative Example 5 except that the starting silane used was triisopropoxysilane, a secondary alkoxysilane, and the reaction temperature was maintained at 140° C. After three hours the reaction was complete as monitored by GPC. The major product formed was vinyltriisopropoxysilane (95%). 1,2-bis(triisopropoxysilyl)ethane (3%) and tetraisopropoxysilane (2%) by-products were also formed.

The triisopropoxysilane employed in this test had a secondary alkyl, not a tertiary group, and the reaction temperature was below the temperature required by the process of the invention.

What is claimed is:

1. Process for preparing vinyl-tri-t-alkoxysilanes by reacting a tri-t-alkoxysilane of the general formula I:

$$HSi(OCRR'R'')_3 \qquad [I]$$

with an alkyne of the general formula II:

$$R'''C\equiv CH \qquad [II]$$

wherein R''' is hydrogen, a saturated or unsaturated aliphatic hydrocarbon radical or an aromatic hydrocarbon radical, R, R' and R'' are the same or different and each is a saturated or unsaturated aliphatic hydrocarbon radical or an aromatic hydrocarbon radical, in the presence of a platinum hydrosilation catalyst at a reaction temperature greater than 150° C. to form a vinyl-tri-t-alkoxysilane of the general formula III:

$$R'''CH=CHSi(OCRR'R'')_3 \qquad [III]$$

wherein R, R' R'' and R''' are as before.

2. The process of claim 1 in which the tri-t-alkoxysilane is a tri-t-butoxysilane.

3. The process of claim 1 in which the tri-t-alkoxysilane is tri(2-methyl-2-butoxy)silane.

4. The process of claim 1 in which the tri-t alkoxysilane is tri(3-methyl-3-pentoxy)silane.

5. The process of claim 1 in which the alkyne is acetylene.

6. The process of claim 1 in which the catalyst is chloroplatinic acid.

7. The process of claim 1 in which the catalyst is bis-(triphenylphosphine) platinum (II) chloride.

8. The process of claim 1 in which the reaction temperature is maintained from about 180° C. to 250° C.

9. The process of claim 1 in which the molar ratio of tri-t-alkoxysilane to alkyne is about 1:1.

10. The process of claim 1 in which the catalyst is employed in amounts from $1.0\times10^{-6}$ mole percent to $5.0\times10^{-2}$ mole percent based on the tri-t-alkoxysilane.

11. The process of claim 1 in which the reaction is carried out in a hydrocarbon solvent.

12. The process of claim 11 in which the solvent is triisopropylbenzene.

* * * * *